United States Patent
Watanabe et al.

(10) Patent No.: US 6,548,450 B1
(45) Date of Patent: Apr. 15, 2003

(54) TETRAZOLINONE DERIVATIVES

(75) Inventors: Yukiyoshi Watanabe, Oayama (JP); Toshio Goto, Kokubunji-machi (JP); Seishi Ito, Oyama (JP); Chieko Ueno, Oyama (JP)

(73) Assignee: Nihon Bayer Agrochem, K.K., Tokyo (JP)

( * ) Notice: Subject to any disclaimer, the term of this patent is extended or adjusted under 35 U.S.C. 154(b) by 0 days.

(21) Appl. No.: 09/980,874

(22) PCT Filed: May 8, 2000

(86) PCT No.: PCT/IB00/00588

§ 371 (c)(1), (2), (4) Date: Nov. 15, 2001

(87) PCT Pub. No.: WO00/00715

PCT Pub. Date: Nov. 30, 2000

(30) Foreign Application Priority Data

May 21, 1999 (JP) ............................................ 11-141800

(51) Int. Cl.$^7$ ............................................ A01N 43/113
(52) U.S. Cl. .................................................... 504/261
(58) Field of Search ........................... 548/251; 504/261

(56) References Cited

U.S. PATENT DOCUMENTS

| | | | |
|---|---|---|---|
| 5,342,954 A | 8/1994 | Goto et al. | 548/251 |
| 5,344,814 A | 9/1994 | Goto et al. | 504/261 |
| 5,347,009 A | 9/1994 | Goto et al. | 548/251 |
| 5,362,704 A | 11/1994 | Goto et al. | 504/134 |
| 5,541,336 A | 7/1996 | Goto et al. | 548/251 |
| 5,589,439 A | 12/1996 | Goto et al. | 504/261 |
| 5,605,920 A | 2/1997 | Goto et al. | 514/381 |
| 5,635,446 A | 6/1997 | Goto et al. | 504/130 |
| 5,641,727 A | 6/1997 | Goto et al. | 504/253 |
| 5,650,374 A | 7/1997 | Goto et al. | 507/130 |
| 5,652,198 A | 7/1997 | Goto et al. | 504/261 |
| 5,654,257 A | 8/1997 | Goto et al. | 504/261 |
| 5,668,087 A | 9/1997 | Goto et al. | 504/247 |
| 5,710,278 A | 1/1998 | Goto et al. | 546/268.4 |
| 4,826,529 A * | 5/1998 | Covey et al. | 71/92 |
| 5,747,420 A | 5/1998 | Goto et al. | 504/209 |
| 5,767,286 A * | 6/1998 | Yanagi et al. | 548/251 |
| 5,776,858 A | 7/1998 | Goto et al. | 504/225 |
| 6,017,853 A | 1/2000 | Goto et al. | 504/271 |
| 6,262,275 B1 | 7/2001 | Goto et al. | 548/247 |

FOREIGN PATENT DOCUMENTS

| | | |
|---|---|---|
| DE | 28 19 873 | 11/1978 |
| EP | 0 146 279 A1 | 6/1985 |
| EP | 0 202 929 | 11/1986 |
| EP | 0 638 561 | 2/1995 |
| EP | 0 643 049 | 3/1995 |
| EP | 0 646 577 | 4/1995 |
| EP | 0 708 097 | 4/1996 |
| EP | 0 820 994 | 1/1998 |
| EP | 2751968 | 2/1998 |
| JP | 7-82258 | 3/1995 |
| JP | 7-97372 | 4/1995 |
| JP | 7-118246 | 5/1995 |
| JP | 8-119948 | 5/1996 |
| JP | 8-119949 | 5/1996 |
| JP | 8-119950 | 5/1996 |
| JP | 8-119951 | 5/1996 |
| JP | 9-100272 | 4/1997 |
| WO | 00/40568 | 7/2000 |

\* cited by examiner

*Primary Examiner*—Joseph K. McKane
*Assistant Examiner*—Jennifer C. Murphy
(74) *Attorney, Agent, or Firm*—Richard E. L. Henderson; Raymond J. Harmuth

(57) ABSTRACT

According to the instant invention there have been found novel tetrazolinone derivatives represented by the general formula (I)

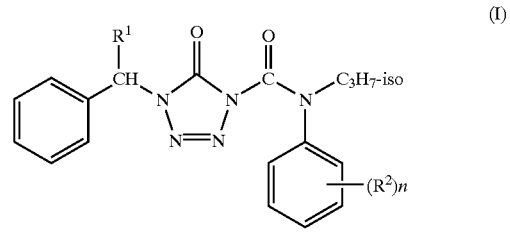

(I)

wherein $R^1$ represents methyl or ethyl, $R^2$ represents halogen, alkyl, haloalkyl, alkoxy, haloalkoxy, alkylthio, haloalkylthio, alkylsulfinyl, alkylsulfonyl, phenyl, phenoxy, alkoxycarbonyl, nitro or cyano, and n represents 0, 1, 2, 3, 4 or 5, processes and intermediates for their preparation and their use as herbicides.

9 Claims, No Drawings

TETRAZOLINONE DERIVATIVES

This is a 371 of PCT/IB00/00588 filed May 8, 2000.

The present invention relates to novel tetrazolinone derivatives, to processes for their preparation and to their use as herbicides.

In Japanese Laid-Open Patent Publications No. 82258/1995, No. 97372/1995 and No. 118246/1995 there are disclosed preparation processes of some tetrazolinone derivatives and a preparation process of 1-substituted-5 (4H)-tetrazolinones, the intermediates thereof. Moreover, the EP-A-146,279 discloses that some tetrazolinone derivatives have herbicidal activities.

However, the known tetrazolinone derivatives are not fully satisfactory with regard to their herbicidal activity and their phytotoxicity against crops.

According to the invention there have now been found novel tetrazolinone derivatives of the general formula (I)

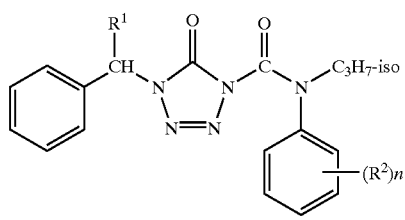

(I)

wherein
R$^1$ represents methyl or ethyl,
R$^2$ represents halogen, alkyl, haloalkyl, alkoxy, haloalkoxy, alkylthio, haloalkylthio, alkylsulfinyl, alkylsulfonyl, phenyl, phenoxy, alkoxycarbonyl, nitro or cyano, and n represents 0, 1, 2, 3, 4 or 5.

The compounds of the formula (I), according to the invention, can be obtained by a process in which
a) compounds of the general formula (II)

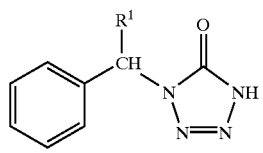

(II)

wherein
R$^1$ is defined as mentioned above, are reacted with compounds of the general formula (III)

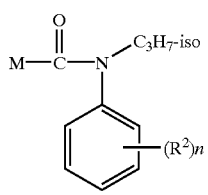

(III)

wherein
R$^2$ and n are defined as mentioned above, and
M represents a leaving group such as chloro or bromo
in the presence of an inert solvent and, if appropriate, in the presence of a base.

The compounds of the formula (I) of the present invention posses strong herbicidal activities and especially demonstrate an excellent herbicidal effect compared with the known compounds described in the aforementioned EP-A-146,279 which are similar to the compounds of the formula (I). The compounds of the invention nevertheless also show a good compatibility with crops. Therefore, the compounds of the present invention can be potentially employed as agrochemicals, specifically as herbicides.

In the formulae mentioned above:
Halogen in "halogen", "haloalkyl", "haloalkoxy" and "haloalkylthio" represents fluoro, chloro, bromo or iodo, and preferably fluoro, chloro or bromo.

"Alkyl" may be straight chain or branched chain and there may be mentioned, for example, methyl, ethyl, n- or isopropyl, n-, iso-, sec- or tert-butyl, n- or iso-pentyl, tert-amyl, pentan-3-yl, neopentyl and n-hexyl.

"Alkoxy" may be straight chain or branched chain and there may be mentioned, for example, methoxy, ethoxy, propoxy, isopropoxy, n-, iso-, sec- or tert-butoxy, n-pentyloxy and n-hexyloxy.

"Alkylthio" may be straight chain or branched chain and there may be mentioned, for example, methylthio, ethylthio, n-propylthio, isopropylthio and n-butylthio.

"Alkylsulfinyl" may be straight chain or branched chain and there may be mentioned, for example, methylsulfinyl, ethylsulfinyl, n-propylsulfinyl, isopropylsulfinyl and n-butylsulfinyl.

"Alkylsulfonyl" may be straight chain or branched chain and there may be mentioned, for example, methylsulfonyl, ethylsulfonyl, n-propylsulfonyl, isopropyl-sulfonyl and n-butylsulfonyl.

"Haloalkyl" may be straight chain or branched chain and there may be mentioned, for example, difluoromethyl, trifluoromethyl, 2-fluoroethyl, 2-chloroethyl, 2-bromoethyl, 2,2,2-trifluoroethyl, 1,1,2,2-tetrafluoroethyl, 1,1,2,2,2-pentafluoroethyl, 2,2,3,3,3-pentafluoropropyl, 3-chloropropyl, 1,3-difluoropropan-2-yl, 1,1,1-trifluoropropan-2-yl, 2,2,3,3,4,4,4-heptafluorobutyl and 3-bromopropyl.

The Haloalkyl part of "haloalkoxy" and "haloalkylthio" may be as defined in the above-mentioned "haloalkyl".

As "alkoxycarbonyl" there may be mentioned, for example, methoxycarbonyl, ethoxycarbonyl, n-propoxycarbonyl, isopropoxycarbonyl and n-butoxycarbonyl.

As a preferable group of compounds of the present invention there can be mentioned the compounds of the aforementioned formula (I) wherein
R$^1$ represents methyl or ethyl,
R$^2$ represents fluoro, chloro, bromo, C$_{1-4}$ alkyl, C$_{1-4}$ haloalkyl, C$_{1-4}$ alkoxy, C$_{1-4}$ haloalkoxy, C$_{1-4}$ alkylthio, C$_{1-4}$ haloalkylthio, C$_{1-4}$ alkylsulfinyl, C$_{1-4}$ alkylsulfonyl, phenyl, phenoxy, C$_{1-4}$ alkoxycarbonyl, nitro or cyano, and n represents 0, 1, 2, 3 or 4.

As a more preferable group of compounds of the present invention there can be mentioned the compounds of the aforementioned formula (I) wherein
R$^1$ represents methyl,
R$^2$ represents fluoro, chloro, methyl, ethyl, n-propyl, isopropyl, tert-butyl, trifluoromethyl, methoxy, ethoxy, isopropoxy, trifluoromethoxy, difluoromethoxy, 2,2,2-trifluoroethoxy, methylthio, ethylthio, isopropylthio, methysulfinyl, methylsulfonyl, phenyl, phenoxy, methoxycarbonyl, ethoxycarbonyl, nitro or cyano, and n represents 0, 1, 2, or 3.

Among the compounds of the aforementioned formula (I) there may be especially pointed out the compounds which are represented by the following formula

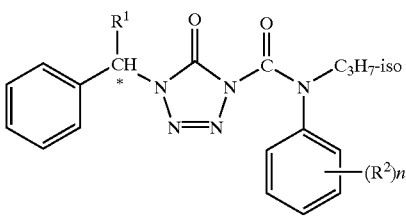

wherein the carbon atom marked with * represents an asymmetric carbon atom and $R^1$ and $R^2$ have the same meaning as mentioned above. Based on this fact the compounds of the present invention can exist as pure optically active enantiomers or in a form of optional mixtures of optically active enantiomers. Therefore, the compounds of the aforementioned formula (I) of the present invention include optically active substances and mixtures thereof.

Using, for example, 1-((S)-α-methylbenzyl)-5(4H)-tetrazolinone and N-isopropyl-N-phenylcarbamoyl chloride as the starting materials according to preparation process a), the said preparation process can be illustrated by the following reaction scheme:

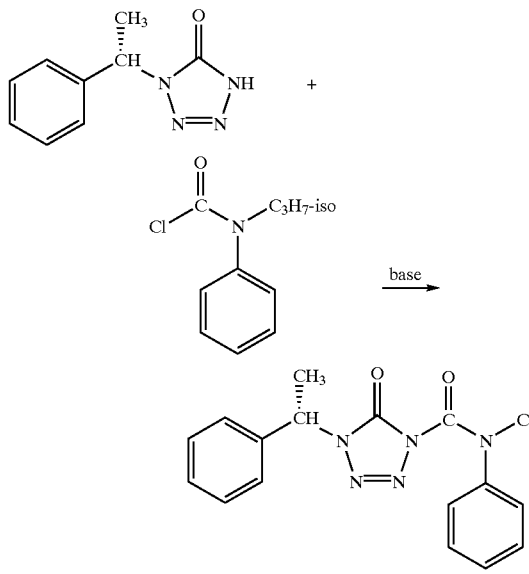

The compounds of the formula (II), which are used as the starting materials in the aforementioned preparation process a) are novel compounds, which were not described in literature, and can be prepared, for example, by the following proccesses in which according to process variant b) compounds of the general formula (IV)

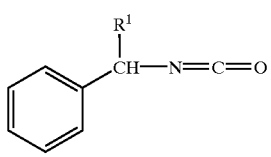

(IV)

wherein
$R^1$ is defined as mentioned above,
are reacted with trimethylsilyl azide in the presence of a catalytic amount of boron trifluoride-ether-complex, or according to process variant c) compounds of the above-mentioned general formula (IV) are reacted with sodium azide in a polar solvent in the presence of a catalytic quantity of aluminium chloride.

The compounds of the general formula (IV) which are used as the starting material in the above-mentioned preparation process variants b) and c) include isocyanates known in the area of organic chemistry and can be easily obtained, for example, by reacting amines of the general formula (V)

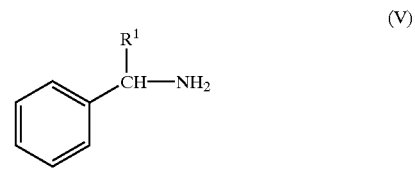

(V)

wherein
$R^1$ is as defined above,
with, for example, phosgene according to known methods described, for example, in "SHIN JIKKEN KAGAKU KOUZA" (New experimental chemistry lecture) Vol. 14, III, pp.1490–1496 (published by Maruzen Ltd. on Feb. 20, 1978).

The compounds of the above-mentioned formula (V) can be synthesized, for example, similarly to the methods described in "SHIN JIKKEN KAGAKU KOUZA" (New experimental chemistry lecture) Vol. 14, III, pp.1332–1398 (published by Maruzen Ltd. on Feb. 20, 1978) or Organic Reactions, Vol. 5, 1949, 301–330 (John Wiley & Sons, Inc.).

As compounds of the above-mentioned formula (II) there can be mentioned the following species:

1-((S)-α-methylbenzyl)-5(4H)-tetrazolinone,
1-((R)-α-methylbenzyl)-5(4H)-tetrazolinone,
1-((S)-α-ethylbenzyl)-5(4H)-tetrazolinone,
1-((R)-α-ethylbenzyl)-5(4H)-tetrazolinone.

The compounds of the formula (III) to be reacted with the compounds of the above-mentioned formula (II) include N-isopropyl-N-(substituted)phenylcarbamoyl halides which are well known in the area of organic chemistry. As typical examples of them there can be mentioned the following compounds:

N-isopropyl-N-phenylcarbamoyl chloride,
N-isopropyl-N-(4-fluorophenyl)carbamoyl chloride,
N-isopropyl-N-(3-methylphenyl)carbamoyl chloride,
N-isopropyl-N-(4-trifluoromethylphenyl)carbamoyl chloride,
N-isopropyl-N-(2-ethoxyphenyl)carbamoyl chloride,
N-isopropyl-N-(4-difluoromethoxyphenyl)carbamoyl chloride,
N-isopropyl-N-(4-isopropylthiophenyl)carbamoyl chloride,
N-isopropyl-N-(4-methylsulfinylphenyl)carbamoyl chloride,
N-isopropyl-N-(4-methylsulfonylphenyl)carbamoyl chloride,
N-isopropyl-N-(4-2,2,2-trifluoroethylthiophenyl) carbamoyl chloride,
N-isopropyl-N-(4-phenylphenyl)carbamoyl chloride,
N-isopropyl-N-(3-phenoxyphenyl)carbamoyl chloride,
N-isopropyl-N-(2-ethoxycarbonylphenyl)carbamoyl chloride,
N-isopropyl-N-(4-nitrophenyl)carbamoyl chloride,
N-isopropyl-N-(4-cyanophenyl)carbamoyl chloride and the bromides corresponding to these chlorides.

The reaction of the preparation process a) is usually conducted in an inert organic solvent. As examples of such inert organic solvents there can be mentioned aliphatic, alicyclic and aromatic hydrocarbons (which may optionally be chlorinated), for example, pentane, hexane, cyclohexane, petroleum ether, ligroine, benzene, toluene, xylene, dichloromethane, chloroform, carbon tetetrachloride, 1,2-dichloroethane, chlorobenzene, dichlorobenzene; ethers, for example, diethyl ether, methyl ethyl ether, diisopropyl ether, dibutyl ether, dioxane, dimethoxyethane (DME), tetra-hydrofuran (THF), diethylene glycol dimethyl ether (DGM); nitriles, for example, acetonitrile, propionitrile; acid amides, for example, dimethylformamide (DMF), dimethylacetamide (DMA), N-methylpyrrolidone, 1,3-dimethyl-2-imidazolidinone, hexamethylphosphoric triamide (HMPA).

The preparation process a) may be conducted in the presence of a base, preferable in the presence of the base 4-dimethylaminopyridine (DMAP).

In case of using DMAP as a base, the reaction of the preparation process a) is usually conducted at about −10 to about 200° C., preferably about 25 to about 140° C. under normal pressure. Optionally it is possible to conduct the reaction under elevated pressure or under reduced pressure.

Moreover, it is possible to conduct the reaction of the preparation process a) using other bases than DMAP. As such bases there can be mentioned inorganic salts (for example, sodium carbonate, potassium carbonate etc.), alkyl alcoholates (for example, sodium methoxide, sodium ethoxide, potassium tert-butoxide), sodium hydroxide, potassium hydroxide, lithium hydroxide, organic bases (for example, triethylamine, 1,1,4,4-tetramethylethylenediamine, N,N-dimethylaniline, pyridine etc.).

In case of conducting said reaction using these bases, the compounds of the formula (I) can be selectively obtained by using DMAP as a catalyst.

The reaction temperature in this case may be in the range of usually about 0 to about 150° C., preferably about 25 to about 100° C. Said reaction is conducted desirably under normal pressure. Optionally, however, it is possible to conduct it under elevated pressure or under reduced pressure.

The desired compounds of the formula (I), according to the present invention, can be obtained, for example, by reacting 1 mole of a compound of the formula (II) with about 1 mole to about 1.5 moles of a compound of the formula (III) in the presence of about 1 mole to about 1.5 moles of DMAP as a base and in such an inert solvent as mentioned above. The compounds of the formula (I) can also be prepared by reacting 1 mole of a compound of the formula (II) with about 1 mole to about 1.5 moles of a compound of the formula (III) in the presence of about 0.01 mole to about 0.3 moles of DMAP as a catalyst and, for example, about 1 mole to about 1.5 moles of potassium carbonate as a base and in an inert solvent of the kind as mentioned above.

The compounds of the formula (I), according to the present invention thus obtained can be isolated and purified, for example, by means of crystallization, chromatography etc.

The reaction of the aforementioned preparation process b) can be conducted using a boron trifluoride-ether-complex as a catalyst. The reaction temperature is usually kept at about 0 to about 200° C., preferably about 50 to about 150° C. The reaction may be conducted desirably under normal pressure. Optionally, however, it is possible to conduct it under elevated pressure or under reduced pressure.

The preparation process b) is usually conducted by reacting 1 mole of a compound of the formula (IV) with about 1 mole to about 2 moles of trimethylsilyl azide in the presence of about 0.005 moles to about 0.01 mole of boron trifluoride-ether-complex as a catalyst.

The reaction of the preparation process c) is usually conducted in a polar solvent. As such polar solvent there can be mentioned, for example, acid amides such as dimethylformamide, dimethylacetamide and sufoxides such as dimethylsulfoxide, sulfolane. The reaction temperature may be generally about 0 to about 200° C., preferably about 20 to about 150° C. The reaction may be conducted desirably under normal pressure. Optionally, however, it is possible to conduct it under elevated pressure or under reduced pressure.

The preparation process c) can be conducted by reacting 1 mole of a compound of the formula (IV) with about 1 mole to about 1.5 moles of sodium azide in the presence of about 0.05 moles to about 1 mole of aluminum chloride as a catalyst and in a polar solvent, for example, dimethylformamide.

The compounds of the formula (I), according to the present invention, have, as shown in the test examples to be described later, excellent herbicidal activities and can be used as herbicidal agents for controlling weeds. "Weeds" in this regard mean, in the broadest sense, all plants which grow in locations where they are undesired.

The compounds, according to the present invention act as total or selective herbicides depending upon the applied concentration. The active compounds of the present invention can be used, for example, as selective herbicides between the following weeds and cultures.

Dicotyledon weeds of the genera: Sinapis, Lepidium, Galium, Stellaria, Chenopodium, Urtica, Senecio, Amaranthus, Portulaca, Xanthium, Ipomoea, Polygonum, Ambrosia, Cirsium, Sonchus, Solanum, Rorippa, Lamium, Veronica, Datura, Viola, Galeopsis, Papaver, Centaurea, Galinsoga, Rotala, Lindemia etc.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita etc.

Monocotyledon weeds of the genera: Echinochloa, Setaria, Panicum, Digitaria, Phleum, Poa, Festuca, Eleusine, Lolium, Bromus, Avena, Cyperus, Sorghum, Agropyron, Monochoria, Fimbristylis, Sagittaria, Eleocharis, Scirpus, Paspalum, Ischaemum, Agrostis, Alopecurus, Cynodon etc.

Monocotyledon cultures of the genera: Oryza, Zea, Triticum, Hordeum, Avena, Secale, Sorghum, Panicum, Saccharum, Ananas, Asparagus, Allium etc.

According to the invention all plants and plant parts can be treated. The term plants includes all plants and plant populations, such as desired or undesired wild plants and cultivated plants (including naturally occurring cultivated varieties). Cultivated plants can be plant varieties that were obtained by conventional breeding and optimizing processes or by biotechnological and genetic engineering methods or a combination of such processes and methods, including transgenic plants and including plant varieties that cannot or can be protected by plant patents or plant variety rights. Plant parts are all parts and organs of plants occurring above or below the surface of the soil, e.g. shoots, leaves, needles, stalks and stems, trunks, flowers, fruits and seeds as well as roots, tubers, bulbs and rhizomes. The term plant parts also includes harvested crops and propagation material, e.g. cuttings, tubers, bulbs, rhizomes, shoots and seeds.

According to the invention the plants and plants parts are treated using the usual methods by applying the active ingredients or compositions containing them directly to the plants or plant parts or to their surroundings (including the soil) or storeroom, e.g. by dipping, spraying, dusting, fogging, spreading and in the case of propagation material also by coating using one or multiple layers.

The use of the compounds of the formula (I), according to the present, invention is not restricted to the above-mentioned plants, but may be applied to other plants in the same manner. The active compounds can, depending upon the applied concentration, non-selectively control weeds and may be used, for example, on industrial terrain, rail tracks, paths, places with or without planted trees.

Moreover, the compounds, according to the present invention, can be used for controlling weeds in perennial cultures and applied in, for example, afforestations, decorative tree plantings, orchards, vineyards, citrus groves, nut orchards, banana plantations, coffee plantations, tea plantations, rubber plantations, oil palm plantations, cocoa plantations, soft fruit plantings, hopfields etc. and can be applied for the selective controlling of weeds in annual cultures.

The compounds of the formula (I), according to the present invention, can be made into customary agrochemical formulations for their application. As such formulations there can be mentioned,-for example, solutions, emulsions, wettable powders, suspensions, powders, soluble powders, granules, tablets, suspension-emulsion concentrates, microcapsules in polymeric substances, jumbo formulations etc.

The formulations can be prepared according to known methods, for example, by mixing the compounds of the formula (I) of the present invention with extenders, namely liquid diluents and/or solid diluents or carriers, optionally with surface-active agents, namely emulsifiers and/or dispersants and/or foam-forming agents. When water is used as an extender, for example, organic solvents can be used as auxiliary solvents.

As liquid diluents or carriers there can be mentioned aromatic hydrocarbons (for example, xylene, toluene, alkylnaphthalene etc.), chlorinated aromatic or chlorinated aliphatic hydrocarbons (for example, chlorobenzenes, ethylene chlorides, methylene chloride etc.), aliphatic hydrocarbons [for example, cyclohexane etc. or paraffins (for example, mineral oil fractions etc.)], alcohols (for example, butanol, glycols and their ethers and esters etc.), ketones (for example, acetone, methyl ethyl ketone, methyl isobutyl ketone, cyclohexanone etc.), strongly polar solvents (for example, dimethylformamide, dimethylsulphoxide etc.) and water.

As solid diluents there can be mentioned, for example, ground natural minerals (for example, kaolin, clay, talc, chalk, quartz, attapulgite, montmorillonite, diatomaceous earth etc.), ground synthetic minerals (for example, highly dispersed silicic acid, alumina, silicates etc.) etc.

As solid carriers for granules there can be mentioned, for example, crushed and fractionated rocks (for example, calcite, marble, pumice, sepiolite, dolomite etc.), synthetic granules of inorganic and organic meals, particles of organic materials (for example, sawdust, coconut shells, maize cobs and tobacco stalks etc.) etc.

As emulsifiers and/or foam-forming agents there can be mentioned nonionic and anionic emulsifiers [for example, polyoxyethylene fatty acid esters, polyoxyethylene fatty acid alcohol ethers (for example, alkylaryl polyglycol ethers, alkylsulphonates, alkylsulphates, arylsulphonates etc.)], albumin hydrolysis products etc.

As dispersants there are included, for example, ligninsulphite waste liquor and methyl cellulose.

Tackifiers may also be used in the formulations (powders, granules, emulsions). As usable tackifiers there can be mentioned, for example, carboxymethyl cellulose, natural and synthetic polymers (for example, gum arabic, polyvinyl alcohol, polyvinyl acetate etc.).

Colorants may also be used. As said colorants there can be mentioned, for example, inorganic pigments (for example, iron oxide, titanium oxide, Prussian Blue etc.), organic dyestuffs such as alizarin dyestuffs, azo dyestuffs or metal phthalocyanine dyestuffs, and further trace nutrients such as salts of metals such as iron, manganese, boron, copper, cobalt, molybdenum, zinc etc.

Said formulations can contain in a range of generally 0.1–95% by weight, preferably 0.5–90% by weight of the compounds of the aforementioned formula (I).

The compounds of the formula (I) of the present invention can be used as such or in their formulated forms for controlling weeds. They can be used also as a mixed composition with known herbicides. Such a mixed composition can be previously prepared as a final formulation form or can be prepared by tank-mixing on the occasion of the application.

The compounds of the formula (I) of the present invention can be used also with a safener and their application as a selective herbicide may be broadened by such a mixing. As an example of such safener 1-($\alpha,\alpha$-dimethylbenzyl)-3-p-tolylurea can be mentioned.

As herbicides, which can be combined with the compounds of the formula (I) of the present invention there can be mentioned, for example, the following known herbicides:

4-amino-6-(1,1-dimethylethyl)-3-ethylthio-1,2,4-triazin-5(4H)-one, 1-amino-6-ethylthio-3-(2,2-dimethylpropyl)-1,3,5-triazin-2,4(1H,3H)-dione, or N-(2-benzothiazolyl)-N,N'-dimethylurea etc. (eg. for controlling weeds in cereal cultures);

4-amino-3-methyl-6-phenyl-1,2,4-triazin-5(4H)-one etc. (e.g. for controlling weeds in sugar cane cultures);

4-amino-6-(1,1-dimethylethyl)-3-methylthio-1,2,4-triazin-5(4H)-one etc. (e.g. for controlling weeds in soybean cultures);

methyl $\alpha$-(4,6-dimethoxypyrimidin-2-ylcarbamoylsulfamoyl)-o-toluate etc. (e.g. for controlling weeds in paddy rice culture).

Surprisingly, some of these herbicidal combinations of these herbicides with compounds of the formula (I) of the present invention show synergistic effects.

Compounds of the formula (I) of the present invention can be applied directly as such or in formulated forms such as ready-to-use solutions, emulsions, suspensions, powders, granules or used in the use forms prepared by further dilution.

The compounds of the formula (I) of the present invention can be applied by means of, for example, watering, spraying, atomizing, dusting or granule application etc.

The compounds of the formula (I) of the present invention can be used at any stages before and after germination of plants. They may also be mixed into the soil before sowing.

The application rate of the compounds of the formula (I) of the present invention may be varied in a substantial range and is fundamentally different according to the nature of the desired effect. In case of herbicidal use, as a suitable application rate there can be mentioned, for example, a range of about 0.01 to about 5 kg, preferably about 0.1 to about 3 kg of the compounds of the formula (I) of the present invention per hectare.

The preparations and applications of the compounds of the present invention are described more specifically in the following examples. However, the present invention should not be restricted to them in any way.

"Parts" mean "parts by weight" unless specified.

SYNTHESIS EXAMPLE 1

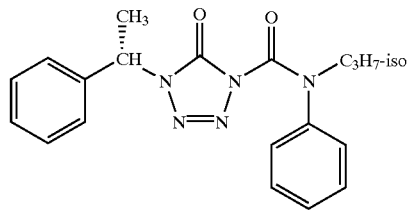

1-((S)-α-methylbenzyl)-5(4H)-tetrazolinon (1.00 g), N,N-dimethylaminopyridine (0.77 g) and N-isopropyl-N-phenylcarbamoyl chloride (1.25 g) were dissolved in toluene (20 ml) and stirred at 80° C. for 8 hours on heating. After naturally cooling the reaction mixture was washed with water (2 times with 10 ml), dried with anhydrous sodium sulfate and then the solvent was distilled off under reduced pressure. The residue was treated by silica gel column chromatography (eluant: hexane: ethyl acetate=3:1) to obtain 1-((S)-α-methylbenzyl)-4-(N-isopropyl-N-phenylcarbamoyl)-5(4H)-tetrazolinone (1.72 g). mp: 79–81° C.

The compounds obtained in the same manner as the above-mentioned Synthesis Example are shown in the following Table 1 together with the compound obtained in the above-mentioned Synthesis Example 1.

TABLE 1

| Compound No. | $R^1$ | $(R^2)n$ | *R/S | Property |
|---|---|---|---|---|
| 1 | $CH_3$ | H | racemate | |
| 2 | $CH_3$ | H | R | mp 79–81° C. |
| 3 | $CH_3$ | H | S | mp 79–81° C. |
| 4 | $CH_3$ | 2-F | racemate | |
| 5 | $CH_3$ | 2-F | R | $n^D_{20}$ 1.5421 |
| 6 | $CH_3$ | 2-F | S | $n^D_{20}$ 1.5386 |
| 7 | $CH_3$ | 3-F | racemate | |
| 8 | $CH_3$ | 3-F | R | mp 84–86° C. |
| 9 | $CH_3$ | 3-F | S | mp 83–85° C. |
| 10 | $CH_3$ | 4-F | racemate | |
| 11 | $CH_3$ | 4-F | R | mp 68–71° C. |
| 12 | $CH_3$ | 4-F | S | mp 67–69° C. |
| 13 | $CH_3$ | 2-Cl | racemate | |
| 14 | $CH_3$ | 2-Cl | R | mp 79–81° C. |
| 15 | $CH_3$ | 2-Cl | S | mp 78–81° C. |
| 16 | $CH_3$ | 3-Cl | racemate | |
| 17 | $CH_3$ | 3-Cl | R | mp 75–77° C. |
| 18 | $CH_3$ | 3-Cl | S | mp 76–78° C. |
| 19 | $CH_3$ | 4-Cl | racemate | |
| 20 | $CH_3$ | 4-Cl | R | mp 68–70° C. |
| 21 | $CH_3$ | 4-Cl | S | mp 68–70° C. |
| 22 | $CH_3$ | 2-Br | racemate | |
| 23 | $CH_3$ | 2-Br | R | |
| 24 | $CH_3$ | 2-Br | S | |
| 25 | $CH_3$ | 3-Br | racemate | |
| 26 | $CH_3$ | 3-Br | R | |
| 27 | $CH_3$ | 3-Br | S | |
| 28 | $CH_3$ | 4-Br | racemate | |
| 29 | $CH_3$ | 2-I | racemate | |
| 30 | $CH_3$ | 3-I | racemate | |
| 31 | $CH_3$ | 4-I | racemate | |
| 32 | $CH_3$ | 4-Br | R | |
| 33 | $CH_3$ | 4-Br | S | |
| 34 | $CH_3$ | 2-$CH_3$ | racemate | |
| 35 | $CH_3$ | 2-$CH_3$ | R | mp 97–100° C. |
| 36 | $CH_3$ | 2-$CH_3$ | S | mp 94–95° C. |
| 37 | $CH_3$ | 3-$CH_3$ | racemate | |
| 38 | $CH_3$ | 3-$CH_3$ | R | mp 48–52° C. |
| 39 | $CH_3$ | 3-$CH_3$ | S | mp 55–58° C. |
| 40 | $CH_3$ | 4-$CH_3$ | racemate | |
| 41 | $CH_3$ | 4-$CH_3$ | R | mp 45–50° C. |
| 42 | $CH_3$ | 4-$CH_3$ | S | mp 44–47° C. |
| 43 | $CH_3$ | 3-$C_2H_5$ | racemate | |
| 44 | $CH_3$ | 4-$C_2H_5$ | racemate | |
| 45 | $CH_3$ | 4-$C_3H_7$-n | racemate | |
| 46 | $CH_3$ | 2-$C_3H_7$-iso | racemate | |
| 47 | $CH_3$ | 4-$C_3H_7$-iso | racemate | |
| 48 | $CH_3$ | 4-$C_4H_9$-tert | racemate | |
| 49 | $CH_3$ | 2-$CF_3$ | racemate | |
| 50 | $CH_3$ | 2-$CF_3$ | R | mp 79–81° C. |
| 51 | $CH_3$ | 2-$CF_3$ | S | mp 78–81° C. |
| 52 | $CH_3$ | 3-$CF_3$ | racemate | |
| 53 | $CH_3$ | 3-$CF_3$ | R | $n^D_{20}$ 1.5209 |
| 54 | $CH_3$ | 3-$CF_3$ | S | $n^D_{20}$ 1.5194 |
| 55 | $CH_3$ | 4-$CF_3$ | racemate | |
| 56 | $CH_3$ | 4-$CF_3$ | R | mp 118–121° C. |
| 57 | $CH_3$ | 4-$CF_3$ | S | mp 116–118° C. |
| 58 | $CH_3$ | 4-$OCH_3$ | racemate | |
| 59 | $CH_3$ | 4-$OCH_3$ | R | |
| 60 | $CH_3$ | 4-$OCH_3$ | S | |
| 61 | $CH_3$ | 2-$OC_2H_5$ | racemate | |
| 62 | $CH_3$ | 3-$OC_2H_5$ | racemate | |
| 63 | $CH_3$ | 4-$OC_2H_5$ | racemate | |
| 64 | $CH_3$ | 4-$OC_3H_7$-iso | racemate | |
| 65 | $CH_3$ | 3-$OCF_3$ | racemate | |
| 66 | $CH_3$ | 4-$OCF_3$ | racemate | |
| 67 | $CH_3$ | 4-$OCHF_2$ | racemate | |
| 68 | $CH_3$ | 4-$OCH_2CF_3$ | racemate | |
| 69 | $CH_3$ | 2-$SCH_3$ | racemate | |
| 70 | $CH_3$ | 3-$SCH_3$ | racemate | |
| 71 | $CH_3$ | 4-$SCH_3$ | racemate | |
| 72 | $CH_3$ | 4-$SC_2H_5$ | racemate | |
| 73 | $CH_3$ | 4-$SC_3H_7$-iso | racemate | |
| 74 | $CH_3$ | 4-$S(O)CH_3$ | racemate | |
| 75 | $CH_3$ | 4-$SO_2CH_3$ | racemate | |
| 76 | $CH_3$ | 4-$SCF_3$ | racemate | |
| 77 | $CH_3$ | 4-$SCH_2CF_3$ | racemate | |
| 78 | $CH_3$ | 4-(phenyl) | racemate | |
| 79 | $CH_3$ | 3-O-(phenyl) | racemate | |

TABLE 1-continued

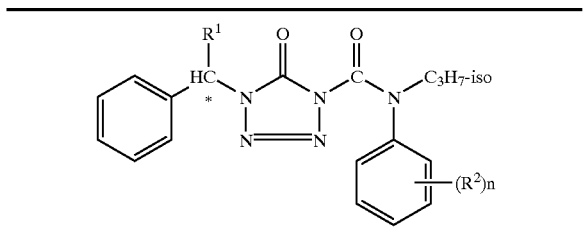

| Compound No. | $R^1$ | $(R^2)n$ | *R/S | Property |
|---|---|---|---|---|
| 80 | $CH_3$ | 4-O-phenyl | racemate | |
| 81 | $CH_3$ | 2-$CO_2CH_3$ | racemate | |
| 82 | $CH_3$ | 2-$CO_2C_2H_5$ | racemate | |
| 83 | $CH_3$ | 4-$NO_2$ | racemate | |
| 84 | $CH_3$ | 4-CN | racemate | |
| 85 | $CH_3$ | 2,3-$F_2$ | racemate | |
| 86 | $CH_3$ | 2,4-$F_2$ | racemate | |
| 87 | $CH_3$ | 2,4-$F_2$ | R | $n^D_{20}$ 1.5319 |
| 88 | $CH_3$ | 2,4-$F_2$ | S | $n^D_{20}$ 1.5329 |
| 89 | $CH_3$ | 2,5-$F_2$ | racemate | |
| 90 | $CH_3$ | 2,6-$F_2$ | racemate | |
| 91 | $CH_3$ | 2,6-$F_2$ | R | mp 56–60° C. |
| 92 | $CH_3$ | 2,6-$F_2$ | S | mp 53–58° C. |
| 93 | $CH_3$ | 3,4-$F_2$ | racemate | |
| 94 | $CH_3$ | 3,4-$F_2$ | R | |
| 95 | $CH_3$ | 3,4-$F_2$ | S | |
| 96 | $CH_3$ | 3,5-$F_2$ | racemate | |
| 97 | $CH_3$ | 2-F, 4-Cl | racemate | |
| 98 | $CH_3$ | 2-F, 4-Br | racemate | |
| 99 | $CH_3$ | 2-F, 5-$CF_3$ | racemate | |
| 100 | $CH_3$ | 2-F, 4-$OCH_3$ | racemate | |
| 101 | $CH_3$ | 3-F, 6-$CF_3$ | racemate | |
| 102 | $CH_3$ | 3-F, 3-$CF_3$ | racemate | |
| 103 | $CH_3$ | 3-F, 4-$CH_3$ | racemate | |
| 104 | $CH_3$ | 3-F, 5-$CH_3$ | racemate | |
| 105 | $CH_3$ | 2,3-$Cl_2$ | racemate | |
| 106 | $CH_3$ | 2,4-$Cl_2$ | racemate | |
| 107 | $CH_3$ | 2,4-$Cl_2$ | R | |
| 108 | $CH_3$ | 2,4-$Cl_2$ | S | |
| 109 | $CH_3$ | 2,6-$Cl_2$ | racemate | |
| 110 | $CH_3$ | 2,5-$Cl_2$ | racemate | |
| 111 | $CH_3$ | 3,4-$Cl_2$ | racemate | |
| 112 | $CH_3$ | 3,5-$Cl_2$ | racemate | |
| 113 | $CH_3$ | 3,4-$Cl_2$ | R | |
| 114 | $CH_3$ | 3,4-$Cl_2$ | S | |
| 115 | $CH_3$ | 2-Cl, 4-F | racemate | |
| 116 | $CH_3$ | 3-Cl, 4-F | racemate | |
| 117 | $CH_3$ | 2-Cl, 4-Br | racemate | |
| 118 | $CH_3$ | 2-Cl, 4-$CH_3$ | racemate | |
| 119 | $CH_3$ | 3-Cl, 4-$CH_3$ | racemate | |
| 120 | $CH_3$ | 3-Cl, 5-$CH_3$ | racemate | |
| 121 | $CH_3$ | 3-Cl, 4-$OCH_3$ | racemate | |
| 122 | $CH_3$ | 2-Br, 4-F | racemate | |
| 123 | $CH_3$ | 2-Br, 4-$CH_3$ | racemate | |
| 124 | $CH_3$ | 2-$CF_3$, 4-F | racemate | |
| 125 | $CH_3$ | 2-$CF_3$, 4-Cl | racemate | |
| 126 | $CH_3$ | 2-$CF_3$, 4-Br | racemate | |
| 127 | $CH_3$ | 3-$CF_3$, 4-F | racemate | |
| 128 | $CH_3$ | 2,3-$(CH_3)_2$ | racemate | |
| 129 | $CH_3$ | 2,4-$(CH_3)_2$ | racemate | |
| 130 | $CH_3$ | 2,4-$(CH_3)_2$ | R | |
| 131 | $CH_3$ | 2,4-$(CH_3)_2$ | S | |
| 132 | $CH_3$ | 2,5-$(CH_3)_2$ | racemate | |
| 133 | $CH_3$ | 2,6-$(CH_3)_2$ | racemate | |
| 134 | $CH_3$ | 3,4-$(CH_3)_2$ | racemate | |
| 135 | $CH_3$ | 3,4-$(CH_3)_2$ | R | |
| 136 | $CH_3$ | 3,4-$(CH_3)_2$ | S | |
| 137 | $CH_3$ | 2-$CH_3$, 6-$C_2H_5$ | racemate | |
| 138 | $CH_3$ | 2-$CH_3$, 3-F | racemate | |
| 139 | $CH_3$ | 2-$CH_3$, 4-F | racemate | |

TABLE 1-continued

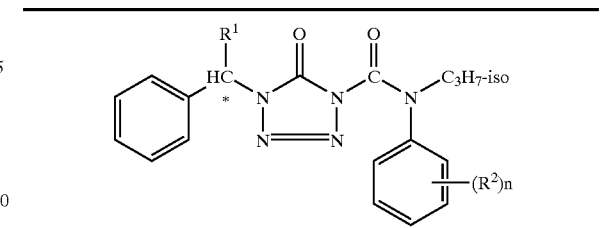

| Compound No. | $R^1$ | $(R^2)n$ | *R/S | Property |
|---|---|---|---|---|
| 140 | $CH_3$ | 2-$CH_3$, 5-F | racemate | |
| 141 | $CH_3$ | 2-$CH_3$, 3-Cl | racemate | |
| 142 | $CH_3$ | 2-$CH_3$, 4-Cl | racemate | |
| 143 | $CH_3$ | 2-$CH_3$, 5-Cl | racemate | |
| 144 | $CH_3$ | 2-$CH_3$, 6-Cl | racemate | |
| 145 | $CH_3$ | 2-$CH_3$, 4-$OCH_3$ | racemate | |
| 146 | $CH_3$ | 2-$CH_3$, 6-$OCH_3$ | racemate | |
| 147 | $CH_3$ | 2,6-$(C_2H_5)_2$ | racemate | |
| 148 | $CH_3$ | 2,5-$(CF_3)_2$ | racemate | |
| 149 | $CH_3$ | 3,5-$(CF_3)_2$ | racemate | |
| 150 | $CH_3$ | 3-$CF_3$, 5-$OCH_3$ | racemate | |
| 151 | $CH_3$ | 3,5-$(CF_3)_2$ | R | |
| 152 | $CH_3$ | 3,5-$(CF_3)_2$ | S | |
| 153 | $CH_3$ | 2,4-$(OCH_3)_2$ | racemate | |
| 154 | $CH_3$ | 3,4-$(OCH_3)_2$ | racemate | |
| 155 | $CH_3$ | 3,4-$(OCH_3)_2$ | R | |
| 156 | $CH_3$ | 3,4-$(OCH_3)_2$ | S | |
| 157 | $CH_3$ | 2-$OCH_3$, 4-F | racemate | |
| 158 | $CH_3$ | 2-$OCH_3$, 5-Cl | racemate | |
| 159 | $CH_3$ | 2-$OCH_3$, 5-$CF_3$ | racemate | |
| 160 | $CH_3$ | 2-$OCH_3$, 5-$CH_3$ | racemate | |
| 161 | $CH_3$ | 2,3,4-$F_3$ | racemate | |
| 162 | $CH_3$ | 2,4,5-$F_3$ | racemate | |
| 163 | $CH_3$ | 2,3,4-$Cl_3$ | racemate | |
| 164 | $CH_3$ | 2,4,6-$(CH_3)_3$ | racemate | |
| 165 | $C_2H_5$ | H | racemate | mp 55–58° C. |
| 166 | $C_2H_5$ | H | R | |
| 167 | $C_2H_5$ | H | S | |
| 168 | $C_2H_5$ | 2-F | racemate | |
| 169 | $C_2H_5$ | 2-F | R | |
| 170 | $C_2H_5$ | 2-F | S | |
| 171 | $C_2H_5$ | 3-F | racemate | |
| 172 | $C_2H_5$ | 3-F | R | |
| 173 | $C_2H_5$ | 3-F | S | |
| 174 | $C_2H_5$ | 4-F | racemate | |
| 175 | $C_2H_5$ | 4-F | R | |
| 176 | $C_2H_5$ | 4-F | S | |
| 177 | $C_2H_5$ | 2-Cl | racemate | |
| 178 | $C_2H_5$ | 2-Cl | R | |
| 179 | $C_2H_5$ | 2-Cl | S | |
| 180 | $C_2H_5$ | 3-Cl | racemate | |
| 181 | $C_2H_5$ | 3-Cl | R | |
| 182 | $C_2H_5$ | 3-Cl | S | |
| 183 | $C_2H_5$ | 4-Cl | racemate | |
| 184 | $C_2H_5$ | 4-Cl | R | |
| 185 | $C_2H_5$ | 4-Cl | S | |
| 186 | $C_2H_5$ | 2-Br | racemate | |
| 187 | $C_2H_5$ | 2-Br | R | |
| 188 | $C_2H_5$ | 2-Br | S | |
| 189 | $C_2H_5$ | 3-Br | racemate | |
| 190 | $C_2H_5$ | 3-Br | R | |
| 191 | $C_2H_5$ | 3-Br | S | |
| 192 | $C_2H_5$ | 4-Br | racemate | |
| 193 | $C_2H_5$ | 2-I | racemate | |
| 194 | $C_2H_5$ | 3-I | racemate | |
| 195 | $C_2H_5$ | 4-I | racemate | |
| 196 | $C_2H_5$ | 4-Br | R | |
| 197 | $C_2H_5$ | 4-Br | S | |
| 198 | $C_2H_5$ | 2-$CH_3$ | racemate | |
| 199 | $C_2H_5$ | 2-$CH_3$ | R | |
| 200 | $C_2H_5$ | 2-$CH_3$ | S | |
| 201 | $C_2H_5$ | 3-$CH_3$ | racemate | |
| 202 | $C_2H_5$ | 3-$CH_3$ | R | |
| 203 | $C_2H_5$ | 3-$CH_3$ | S | |
| 204 | $C_2H_5$ | 4-$CH_3$ | racemate | |

TABLE 1-continued

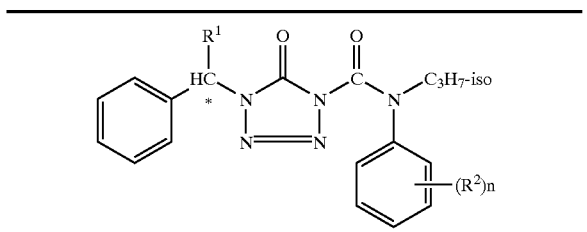

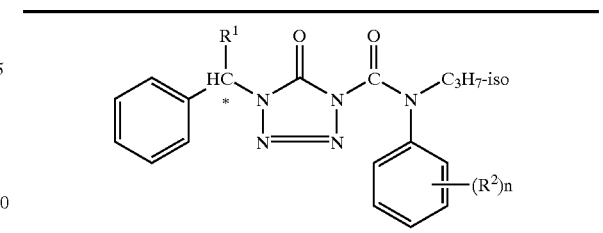

| Compound No. | R¹ | (R²)n | *R/S | Property |
|---|---|---|---|---|
| 205 | $C_2H_5$ | 4-$CH_3$ | R | |
| 206 | $C_2H_5$ | 4-$CH_3$ | S | |
| 207 | $C_2H_5$ | 3-$C_2H_5$ | racemate | |
| 208 | $C_2H_5$ | 4-$C_2H_5$ | racemate | |
| 209 | $C_2H_5$ | 4-$C_3H_7$-n | racemate | |
| 210 | $C_2H_5$ | 2-$C_3H_7$-iso | racemate | |
| 211 | $C_2H_5$ | 4-$C_3H_7$-iso | racemate | |
| 212 | $C_2H_5$ | 4-$C_4H_9$-tert | racemate | |
| 213 | $C_2H_5$ | 3-$CF_3$ | racemate | |
| 214 | $C_2H_5$ | 3-$CF_3$ | R | |
| 215 | $C_2H_5$ | 3-$CF_3$ | S | |
| 216 | $C_2H_5$ | 4-$CF_3$ | racemate | |
| 217 | $C_2H_5$ | 4-$CF_3$ | R | |
| 218 | $C_2H_5$ | 4-$CF_3$ | S | |
| 219 | $C_2H_5$ | 4-$OCH_3$ | racemate | |
| 220 | $C_2H_5$ | 4-$OCH_3$ | R | |
| 221 | $C_2H_5$ | 4-$OCH_3$ | S | |
| 222 | $C_2H_5$ | 2-$OC_2H_5$ | racemate | |
| 223 | $C_2H_5$ | 3-$OC_2H_5$ | racemate | |
| 224 | $C_2H_5$ | 4-$OC_2H_5$ | racemate | |
| 225 | $C_2H_5$ | 4-$OC_3H_7$-iso | racemate | |
| 226 | $C_2H_5$ | 3-$OCF_3$ | racemate | |
| 227 | $C_2H_5$ | 4-$OCF_3$ | racemate | |
| 228 | $C_2H_5$ | 4-$OCHF_2$ | racemate | |
| 229 | $C_2H_5$ | 4-$OCH_2CF_3$ | racemate | |
| 230 | $C_2H_5$ | 2-$SCH_3$ | racemate | |
| 231 | $C_2H_5$ | 3-$SCH_3$ | racemate | |
| 232 | $C_2H_5$ | 4-$SCH_3$ | racemate | |
| 233 | $C_2H_5$ | 4-$SC_2H_5$ | racemate | |
| 234 | $C_2H_5$ | 4-$SC_3H_7$-iso | racemate | |
| 235 | $C_2H_5$ | 4-S(O)$CH_3$ | racemate | |
| 236 | $C_2H_5$ | 4-$SO_2CH_3$ | racemate | |
| 237 | $C_2H_5$ | 3-$SCF_3$ | racemate | |
| 238 | $C_2H_5$ | 4-$SCH_2CF_3$ | racemate | |
| 239 | $C_2H_5$ | 4-phenoxyphenyl | racemate | |
| 240 | $C_2H_5$ | 3-O-phenyl | racemate | |
| 241 | $C_2H_5$ | 4-O-phenyl | racemate | |
| 242 | $C_2H_5$ | 2-$CO_2CH_3$ | racemate | |
| 243 | $C_2H_5$ | 2-$CO_2C_2H_5$ | racemate | |
| 244 | $C_2H_5$ | 4-$NO_2$ | racemate | |
| 245 | $C_2H_5$ | 4-CN | racemate | |
| 246 | $C_2H_5$ | 2,3-$F_2$ | racemate | |
| 247 | $C_2H_5$ | 2,4-$F_2$ | racemate | |
| 248 | $C_2H_5$ | 2,4-$F_2$ | R | |
| 249 | $C_2H_5$ | 2,4-$F_2$ | S | |
| 250 | $C_2H_5$ | 2,5-$F_2$ | racemate | |
| 251 | $C_2H_5$ | 2,6-$F_2$ | racemate | |
| 252 | $C_2H_5$ | 3,4-$F_2$ | racemate | |
| 253 | $C_2H_5$ | 3,4-$F_2$ | R | |
| 254 | $C_2H_5$ | 3,4-$F_2$ | S | |
| 255 | $C_2H_5$ | 3,5-$F_2$ | racemate | |
| 256 | $C_2H_5$ | 2-F, 4-Cl | racemate | |
| 257 | $C_2H_5$ | 2-F, 4-Br | racemate | |
| 258 | $C_2H_5$ | 2-F, 5-$CF_3$ | racemate | |
| 259 | $C_2H_5$ | 2-F, 4-$OCH_3$ | racemate | |
| 260 | $C_2H_5$ | 3-F, 6-$CF_3$ | racemate | |
| 261 | $C_2H_5$ | 3-F, 3-$CF_3$ | racemate | |
| 262 | $C_2H_5$ | 3-F, 4-$CH_3$ | racemate | |
| 263 | $C_2H_5$ | 3-F, 5-$CH_3$ | racemate | |
| 264 | $C_2H_5$ | 2,3-$Cl_2$ | racemate | |
| 265 | $C_2H_5$ | 2,4-$Cl_2$ | racemate | |
| 266 | $C_2H_5$ | 2,4-$Cl_2$ | R | |
| 267 | $C_2H_5$ | 2,4-$Cl_2$ | S | |
| 268 | $C_2H_5$ | 2,6-$Cl_2$ | racemate | |
| 269 | $C_2H_5$ | 2,5-$Cl_2$ | racemate | |
| 270 | $C_2H_5$ | 3,4-$Cl_2$ | racemate | |
| 271 | $C_2H_5$ | 3,5-$Cl_2$ | racemate | |
| 272 | $C_2H_5$ | 3,4-$Cl_2$ | R | |
| 273 | $C_2H_5$ | 3,4-$Cl_2$ | S | |
| 274 | $C_2H_5$ | 2-Cl, 4-F | racemate | |
| 275 | $C_2H_5$ | 3-Cl, 4-F | racemate | |
| 276 | $C_2H_5$ | 2-Cl, 4-Br | racemate | |
| 277 | $C_2H_5$ | 2-Cl, 4-$CH_3$ | racemate | |
| 278 | $C_2H_5$ | 3-Cl, 4-$CH_3$ | racemate | |
| 279 | $C_2H_5$ | 3-Cl, 5-$CH_3$ | racemate | |
| 280 | $C_2H_5$ | 3-Cl, 4-$CH_3O$ | racemate | |
| 281 | $C_2H_5$ | 2-Br, 4-F | racemate | |
| 282 | $C_2H_5$ | 2-Br, 4-$CH_3$ | racemate | |
| 283 | $C_2H_5$ | 2-$CF_3$, 4-F | racemate | |
| 284 | $C_2H_5$ | 2-$CF_3$, 4-Cl | racemate | |
| 285 | $C_2H_5$ | 2-$CF_3$, 4-Br | racemate | |
| 286 | $C_2H_5$ | 3-$CF_3$, 4-F | racemate | |
| 287 | $C_2H_5$ | 2,3-$(CH_3)_2$ | racemate | |
| 288 | $C_2H_5$ | 2,4-$(CH_3)_2$ | racemate | |
| 289 | $C_2H_5$ | 2,4-$(CH_3)_2$ | R | |
| 290 | $C_2H_5$ | 2,4-$(CH_3)_2$ | S | |
| 291 | $C_2H_5$ | 2,5-$(CH_3)_2$ | racemate | |
| 292 | $C_2H_5$ | 2,6-$(CH_3)_2$ | racemate | |
| 293 | $C_2H_5$ | 3,4-$(CH_3)_2$ | racemate | |
| 294 | $C_2H_5$ | 3,4-$(CH_3)_2$ | R | |
| 295 | $C_2H_5$ | 3,4-$(CH_3)_2$ | S | |
| 296 | $C_2H_5$ | 2-$CH_3$, 6-$C_2H_5$ | racemate | |
| 297 | $C_2H_5$ | 2-$CH_3$, 3-F | racemate | |
| 298 | $C_2H_5$ | 2-$CH_3$, 4-F | racemate | |
| 299 | $C_2H_5$ | 2-$CH_3$, 5-F | racemate | |
| 300 | $C_2H_5$ | 2-$CH_3$, 3-Cl | racemate | |
| 301 | $C_2H_5$ | 2-$CH_3$, 4-Cl | racemate | |
| 302 | $C_2H_5$ | 2-$CH_3$, 5-Cl | racemate | |
| 303 | $C_2H_5$ | 2-$CH_3$, 6-Cl | racemate | |
| 304 | $C_2H_5$ | 2-$CH_3$, 4-$OCH_3$ | racemate | |
| 305 | $C_2H_5$ | 2-$CH_3$, 6-$OCH_3$ | racemate | |
| 306 | $C_2H_5$ | 2,6-$(C_2H_5)_2$ | racemate | |
| 307 | $C_2H_5$ | 2,5-$(CF_3)_2$ | racemate | |
| 308 | $C_2H_5$ | 3,5-$(CF_3)_2$ | racemate | |
| 309 | $C_2H_5$ | 3-$CF_3$, 5-$OCH_3$ | racemate | |
| 310 | $C_2H_5$ | 3,5-$(CF_3)_2$ | R | |
| 311 | $C_2H_5$ | 3,5-$(CF_3)_2$ | S | |
| 312 | $C_2H_5$ | 2,4-$(OCH_3)_2$ | racemate | |
| 313 | $C_2H_5$ | 3,4-$(OCH_3)_2$ | racemate | |
| 314 | $C_2H_5$ | 3,4-$(OCH_3)_2$ | R | |
| 315 | $C_2H_5$ | 3,4-$(OCH_3)_2$ | S | |
| 316 | $C_2H_5$ | 2-$OCH_3$, 4-F | racemate | |
| 317 | $C_2H_5$ | 2-$OCH_3$, 5-Cl | racemate | |
| 318 | $C_2H_5$ | 2-$OCH_3$, 5-$CF_3$ | racemate | |
| 319 | $C_2H_5$ | 2-$OCH_3$, 5-$CH_3$ | racemate | |
| 320 | $C_2H_5$ | 2,3,4-$F_3$ | racemate | |

TABLE 1-continued

[Structure: phenyl-HC(R¹)-N(tetrazolinone)-C(=O)-N(C₃H₇-iso)-phenyl-(R²)n]

| Compound No. | R¹ | (R²)n | *R/S | Property |
|---|---|---|---|---|
| 321 | C₂H₅ | 2,4,5-F₃ | racemate | |
| 322 | C₂H₅ | 2,3,4-Cl₃ | racemate | |
| 323 | C₂H₅ | 2,4,6-(CH₃)₃ | racemate | |

SYNTHESIS EXAMPLE 2

(Intermediate)

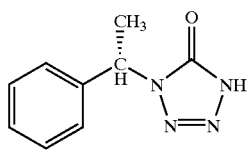

(S)-α-methylbenzyl isocyanate (8.00 g), trimethylsilyl azide (9.40 g) and a catalytic amount of boron trifluoride-ether-complex were mixed and refluxed for 16 hours on heating. The excess amount of trimethylsilyl azide was distilled off under reduced pressure and the residue was treated by silica gel column chromatography (eluant: hexane: ethyl acetate=3:2) to obtain 1-((S)-α-methylbenzyl)-5-(4H)-tetrazolinone (8.18 g). mp: 102–106° C.

SYNTHESIS EXAMPLE 3

(Intermediate)

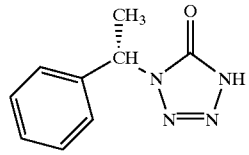

Sodium azide (1.95 g) was suspended in anhydrous dimethylformamide (18 ml) and anhydrous aluminium chloride (0.2 g) was added in an argon stream under ice cooling and stirred for 15 minutes. Then (S)-α-methylbenzyl isocyanate (4.85 g) was added drop by drop and the reaction mixture was stirred for 3 hours in argon stream on heating at 70–75° C. After natural cooling, the reaction mixture was added to a mixture of sodium sulfite (0.5 g), water (100 ml) and ice (50 g) on stirring, acidified with 10% hydrochloric acid and extracted with ethyl acetate. After drying the organic layer with anhydrous sodium sulfate, the solvent was distilled off under reduced pressure and the residue was treated by silica gel column chromatography (eluant: hexane: ethyl acetate= 3:2) to obtain 1-((S)-α-methylbenzyl)-5(4H)-tetrazolinone (3.20 g). mp: 102–106° C.

The compounds obtained according in a similar way as the above-mentioned Synthesis Examples 2 or 3 are listed in the following Table 2 together with the compounds obtained in the Synthesis Examples 2 and 3.

TABLE 2

[Structure: phenyl-C*H(R¹)-N(tetrazolinone-NH)]

| Compound No. | R¹ | *R/S | Property |
|---|---|---|---|
| II-1 | CH₃ | racemate | |
| II-2 | CH₃ | R | mp 97–106° C. |
| II-3 | CH₃ | S | mp 102–106° C. |
| II-4 | C₂H₅ | racemate | mp 103–106° C. |
| II-5 | C₂H₅ | R | |
| II-6 | C₂H₅ | S | |

TEST EXAMPLE 1

Test for Herbicidal Effect Against Paddy Field Weeds

Preparation of formulation of the active compound

Carrier: Acetone 5 parts by weight

Emulsifier: Benzyloxypolyglycolether 1 part by weight

A formulation of the active compound is obtained as an emulsion by mixing 1 part by weight of the active compound with the above-mentioned amount of carrier and emulsifier. A prescribed amount of said formulation is diluted with water to prepare a formulation for testing.

Test method

In a greenhouse 3 seedlings of paddy rice (cultivar: Nipponbare) of 2.5 leafstage (15 cm tall) were transplanted in a 500 cm² pot filled with paddy field soil. Then seeds of barnyard grass, smallflower, bulrush, monochoria and broad-leaved weeds (common false pimpernel, Indian toothcup, long stemmed water wort, Ammannia multiflora Roxb., Dopatrium junceum Hammilt etc.) were sown and water was poured on the soil to a depth of about 2–3 cm.

5 days after the rice transplantation a formulation of each active compound prepared according to the aforementioned preparation method was applied to the surface of the water. A water depth of 3 cm was maintained. The herbicidal effect was examined after 3 weeks from the treatment. The herbicidal effect was rated as 100% in the case of complete death and as 0% in the case of no herbicidal effect.

As a result, the compounds No. 2, 3, 11, 12, 42, 88 and 165 of the present invention showed at an application rate of 0.5 kg/ha sufficient herbicidal effect against paddy field weeds and showed safety to the transplanted paddy rice.

FORMULATION EXAMPLE 1

Granule

To a mixture of 5 parts by weight of compound No. 165, 30 parts by weight of bentonite (montmorillonite), 58 parts by weight of talc and 2 parts by weight of ligninsulphonate, 25 parts by weight of water were added. The mixture is well kneaded, made into granules of 10–40 mesh by extrusion granulation and dried at 40–50° C. to obtain granules.

FORMULATION EXAMPLE 2

Granule 95 parts by weight of clay mineral particles having a particle size distribution of 0.2–2 mm are put in a rotary mixer. While rotating it, 5 parts by weight of the compound No. 2 are sprayed together with a liquid diluent into the mixer, wetted uniformly and dried at 40–50° C. to obtain granules.

FORMULATION EXAMPLE 3

Emulsifiable Concentrate 30 parts by weight of the compound No. 3, 5 parts by weight of xylene, 8 parts by weight of polyoxyethylenealkyl phenyl ether and 7 parts by weight of calcium alkylbenzenesulphonate are mixed and stirred to obtain an emulsion.

FORMULATION EXAMPLE 4

Wettable Powder 15 parts by weight of the compound No. 42, 80 parts by weight of a mixture of white carbon (hydrous amorphous silicon oxide fine particles) and powder clay (1:5), 2 parts by weight of sodium alkylbenzenesulphonate and 3 parts by weight of sodium alkylnaphthalenesulphonate-formalin-polymer are mixed in powder form and made into a wettable powder.

FORMULATION EXAMPLE 5

Water Dispersible Granule 20 parts by weight of the compound No. 2, 30 parts by weight of sodium ligninsulphonate, 15 parts by weight of bentonite and 35 parts by weight of calcined diatomaceous earth powder are well mixed, added with water, then extruded using a 0.3 mm screen and dried to obtain a water dispersible granule.

What is claimed is:

1. A compound according to the Formula (I)

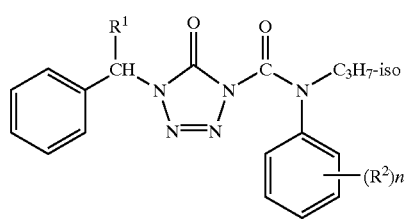

(I)

wherein
  $R^1$ represents methyl or ethyl,
  $R^2$ represents halogen, alkyl, haloalkyl, alkoxy, haloalkoxy, alkylthio, haloalkylthio, alkylsulfinyl, alkylsulfonyl, phenyl, phenoxy, alkoxycarbonyl, nitro or cyano, and
  n represents 0, 1, 2, 3, 4 or 5.

2. The compound according to claim 1 wherein
  $R^1$ represents methyl or ethyl,
  $R^2$ represents fluoro, chloro, bromo, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ alkylsulfinyl, $C_{1-4}$ alkylsulfonyl, phenyl, phenoxy, $C_{1-4}$ alkoxycarbonyl, nitro or cyano, and
  n represents 0, 1, 2, 3 or 4.

3. The compound according to claim 1 wherein
  $R^1$ represents methyl,
  $R^2$ represents fluoro, chloro, methyl, ethyl, n-propyl, isopropyl, tertbutyl, trifluoromethyl, methoxy, ethoxy, isopropoxy, trifluoromethoxy, difluoromethoxy, 2,2,2-trifluoroethoxy, methylthio, ethylthio, isopropylthio, methylsulfinyl, methylsulfonyl, phenyl, phenoxy, methoxycarbonyl, ethoxycarbonyl, nitro or cyano, and
  n represents 0,1,2, or 3.

4. A process for the preparation of a compound of the Formula (I)

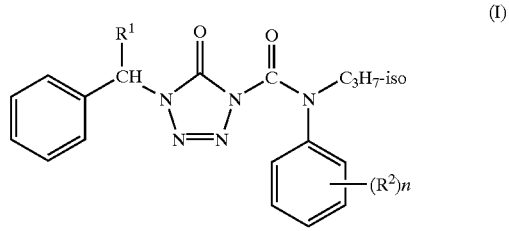

(I)

wherein
  $R^1$ represents methyl or ethyl,
  $R^2$ represents halogen, alkyl, haloalkyl, alkoxy, haloalkoxy, alkylthio, haloalkylthio, alkylsulfinyl, alkylsulfonyl, phenyl, phenoxy, alkoxycarbonyl, nitro or cyano, and
  n represents 0, 1, 2, 3, 4 or 5,
  comprising the step of:
  a) reacting a compound of the Formula (II)

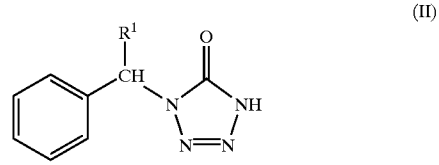

(II)

wherein
  $R^1$ is as defined above, with a compound of the Formula (III)

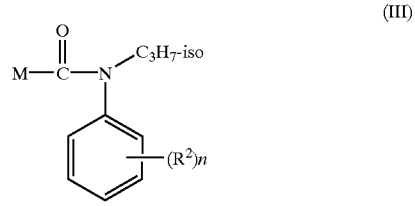

(III)

wherein
  $R^2$ and n are as defined above, and
  M represents a leaving group in the presence of an inert solvent and, optionally, in the presence of a base.

5. An herbicidal composition comprising a compound of the Formula (I) according to claim 1 and a herbicidally acceptable carrier.

6. A process for controlling weeds comprising the step of allowing an effective amount of a compound of the Formula (I) according to claim 1 to act on a member selected from the group consisting of weeds, a habitat of said weeds, and combinations thereof.

7. A process for controlling weeds comprising the step of allowing an effective amount of a herbicidal composition to act on a member selected from the group consisting of weeds, a habitat of said weeds and combinations thereof, wherein said herbicidal composition comprises a compound of the Formula (I) according to claim 1 and a member selected from the group consisting of an extender, a surfactant and combinations thereof.

8. A process for the preparation of a herbicidal composition comprising the step of mixing a compound of the Formula (I) according to claim 1 with a member selected from the group consisting of an extender, a surface active agent and combinations thereof.

9. The process of claim 4, wherein said leaving group of radical M is selected from the group consisting of chloro and bromo.

* * * * *